US00PP30475P2

(12) United States Plant Patent
Arts

(10) Patent No.: US PP30,475 P2
(45) Date of Patent: May 7, 2019

(54) ***HYDRANGEA* PLANT NAMED 'HP217903'**

(50) Latin Name: *Hydrangea paniculata*
Varietal Denomination: HP217903

(71) Applicant: HYDRANGEA BREEDERS ASSOCIATION B.V., De Kwakel (NL)

(72) Inventor: Niels Arts, Aalsmeer (NL)

(73) Assignee: Hydrangea Breeders Association B.V., De Kwakel (NL)

( * ) Notice: Subject to any disclaimer, the term of this patent is extended or adjusted under 35 U.S.C. 154(b) by 0 days.

(21) Appl. No.: 15/932,546

(22) Filed: Mar. 13, 2018

(51) Int. Cl.
*A01H 5/02* (2018.01)

(52) U.S. Cl.
USPC ..... Plt./250

(58) Field of Classification Search
USPC ..... Plt./250
See application file for complete search history.

*Primary Examiner* — Annette H Para
(74) *Attorney, Agent, or Firm* — C. A. Whealy

(57) ABSTRACT

A new and distinct cultivar of *Hydrangea* plant named 'HP217903', characterized by its compact, upright and rounded to conical plant habit; moderately vigorous growth habit and moderate growth rate; freely branching habit with strong, thick and sturdy stems that are dark greyed-red in color; freely and uniformly flowering habit; pyramidal inflorescences with numerous light yellow green-colored sterile flowers; and good garden performance.

3 Drawing Sheets

Botanical designation: *Hydrangea paniculata.*
Cultivar denomination: 'HP217903'.

CROSS-REFERENCED TO CLOSELY-RELATED APPLICATIONS

Title: *Hydrangea* Plant Named 'HP217904'
Applicant: Niels Arts
Filed: Concurrently with this application

BACKGROUND OF THE INVENTION

The present invention relates to a new and distinct cultivar of *Hydrangea* plant, botanically known as *Hydrangea paniculata*, commercially referred to as a panicle *Hydrangea* and hereinafter referred to by the name 'HP217903'.

The new *Hydrangea* plant is a product of a planned breeding program conducted by the Inventor in De Kwakel, The Netherlands and Lengerich, Germany. The objective of the breeding program was to create new compact and freely-branching *Hydrangea* plants with strong sturdy stems, large inflorescences with numerous showy sterile flowers, attractive sterile flower color and good garden performance.

The new *Hydrangea* plant originated from a cross-pollination made by the Inventor in August, 2010 in De Kwakel, The Netherlands, of a proprietary selection of *Hydrangea paniculata* identified as code number 11-0003, not patented, as the female, or seed, parent with a proprietary selection of *Hydrangea paniculata* identified as code number 11-0001, not patented, as the male, or pollen, patent. The new *Hydrangea* plant was discovered and selected by the Inventor as a single flowering plant from within the progeny of the stated cross-pollination in a controlled greenhouse environment in Lengerich, Germany in September, 2012.

Asexual reproduction of the new *Hydrangea* plant by vegetative tip cuttings in a controlled environment in De Kwakel, The Netherlands since March, 2014 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HP217903'. These characteristics in combination distinguish 'HP217903' as a new and distinct *Hydrangea* plant:

1. Compact, upright and rounded to conical plant habit.
2. Moderately vigorous growth habit and moderate growth rate.
3. Freely branching habit with strong, thick and sturdy stems that are dark greyed-red in color.
4. Freely and uniformly flowering habit.
5. Pyramidal inflorescences with numerous light yellow green-colored sterile flowers.
6. Good garden performance.

Plants of the new *Hydrangea* can be compared to plants of the female parent selection. Plants of the new *Hydrangea* differ primarily from plants of the female parent selection in plant habit as plants of the new *Hydrangea* are more compact than plants of the female parent selection. In addition, inflorescences of plants of the new *Hydrangea* have more fertile flowers and are more open than inflorescences of plants of the female parent selection.

Plants of the new *Hydrangea* can be compared to plants of the male parent selection. Plants of the new *Hydrangea* differ primarily from plants of the male parent selection in sterile flower color as plants of the male parent selection have pink-colored sterile flowers.

Plants of the new *Hydrangea* can be compared to plants of the *Hydrangea paniculata* 'HP217904', disclosed in a U.S. Plant Patent application filed concurrently. In side-by-side comparisons, plants of the new *Hydrangea* differ primarily from plants of 'HP217904' in the following characteristics:

1. Plants of the new *Hydrangea* have shorter leaves than plants of 'HP217904'.
2. Inflorescences of plants of the new *Hydrangea* are smaller and have fewer fertile flowers than inflorescences of plants of 'HP217904'.
3. Sterile flowers of plants of the new *Hydrangea* are slightly larger and lighter yellow green than sterile flowers of plants of 'HP217904'.

Plants of the new *Hydrangea* can also be compared to plants of the *Hydrangea paniculata* 'Limelight', disclosed in U.S. Plant Pat. No. 12,874. In side-by-side comparisons, plants of the new *Hydrangea* differ primarily from plants of 'Limelight' in the following characteristics:

1. Plants of the new *Hydrangea* are more conical and narrower in shape than plants of 'Limelight'.
2. Lateral branches of plants of the new *Hydrangea* are darker in color than lateral branches of plants of 'Limelight'.
3. Inflorescences of plants of the new *Hydrangea* have more fertile flowers, fewer sterile flowers and are more open than inflorescences of plants of 'Limelight'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet is a side perspective view of a typical flowering plant of 'HP217903'.

The photograph on the second sheet is a top perspective view of a typical flowering plant of 'HP217903'.

The photograph on the third sheet is a close-up view of typical inflorescences of 'HP217903'.

DETAILED BOTANICAL DESCRIPTION

Plants used in the aforementioned photographs and in the following description were grown during the late summer in 22-cm containers in an outdoor nursery in Lengerich, Germany and under cultural practices typical of commercial panicle *Hydrangea* production. During the production of the plants, day and night temperatures averaged 15° C. Plants of the new *Hydrangea* 18 months old when the photographs and description were taken. In the following description, color references are made to The Royal Horticultural Society Colour Chart, 2015 Edition, except where general terms of ordinary dictionary significance are used.

Botanical description: *Hydrangea paniculata* 'HP217903'.

Parentage:

*Female, or seed, parent.*—Proprietary selection of *Hydrangea paniculata* identified as code number 11-0003, not patented.

*Male, or pollen, parent.*—Proprietary selection of *Hydrangea paniculata* identified as code number 11-0001, not patented.

Propagation:

*Type cutting.*—By vegetative tip cuttings.

*Time to initiate roots, summer.*—About two weeks at temperatures about 23° C.

*Time to initiate roots, winter.*—About 18 days at temperatures about 18° C.

*Time to produce a rooted young plant, summer.*—About four weeks at temperatures about 23° C.

*Time to produce a rooted young plant, winter.*—About five weeks at temperatures about 18° C.

*Root description.*—Thick; typically whitish brown in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Compact, upright and rounded to conical plant habit; strong and sturdy stems; moderately vigorous growth habit and moderate growth rate.

*Plant height.*—About 60 cm to 70 cm.

*Plant diameter or area of spread.*—About 55 cm to 60 cm.

Lateral branch description:

*Branching habit.*—Freely branching habit; when pinched, about 16 lateral branches develop per plant.

*Length.*—About 40 cm to 45 cm.

*Diameter.*—About 5 mm to 7 mm.

*Internode length.*—About 3.5 cm to 5 cm.

*Texture.*—Smooth, glabrous; fully developed, woody.

*Aspect.*—Mostly upright.

*Strength.*—Strong, sturdy.

*Color.*—When developing: Close to 145B; lenticels, close to 165C. Developed: Close to 178A; lenticels, close to 165C.

Leaf description:

*Arrangement.*—Opposite, simple.

*Length.*—About 6 cm to 10 cm.

*Width.*—About 3.5 cm to 6 cm.

*Shape.*—Ovate.

*Apex.*—Acute.

*Base.*—Obtuse.

*Margin.*—Serrulate.

*Texture, upper surface.*—Rugose; pubescent.

*Texture, lower surface.*—Prominent venation; glabrous.

*Venation pattern.*—Pinnate.

*Color.*—Developing leaves, upper surface: Close to 138A. Developing leaves, lower surface: Close to 138B. Fully developed leaves, upper surface: Close to 137B; venation, close to 144B. Fully developed leaves, lower surface: Close to 138B; venation, close to 145C.

*Petioles.*—Length: About 1 cm to 1.5 cm. Diameter: About 2 mm. Texture, upper and lower surfaces: Smooth, glabrous. Color, upper surface: Close to 144B tinged with close to 178B. Color, lower surface: Close to 145C tinged with close to 178B.

Flower description:

*Flower type and habit.*—Showy sterile flowers and small fertile flowers arranged on terminal panicles; panicles pyramidal in shape; flowers face upright to outwardly depending on their position in the inflorescence.

*Fragrance*.—None detected.

*Natural flowering season*.—Plants begin flowering about 18 weeks after planting; flowering begins in the early summer and is continuous throughout the summer in Northern Europe.

*Flower longevity*.—Fertile flowers last about one month on the plant, fertile flowers not persistent; sterile flowers last about three months on the plant, sterile flowers persistent.

*Quantity of flowers*.—Freely flowering habit; about 300 to 400 fertile flowers per panicle and about 100 to 130 sterile flowers per panicle.

*Panicle height*.—About 15 cm to 20 cm.

*Panicle diameter*.—About 12 cm to 14 cm.

*Fertile flower buds*.—Length: About 3 mm. Diameter: About 2 mm. Shape: Rounded. Color: Close to 145A.

*Sterile flower buds*.—Length: About 3 mm. Diameter: About 2 mm. Shape: Rounded. Color: Close to 145A.

*Fertile flower diameter*.—About 3 mm.

*Fertile flower depth* (*height*).—About 3 mm.

*Sterile flower diameter*.—About 2 cm to 4 cm.

*Sterile flower depth* (*height*).—About 3 cm.

*Petals, fertile flowers*.—Quantity and arrangement: About four or five in a single whorl. Length: About 3 mm. Width: About 2 mm. Shape: Ovate. Apex: Acute. Base: Obtuse. Margin: Entire. Texture, upper and lower surfaces: Smooth, glabrous. Color: When opening, upper and lower surfaces: Close to 157D. Fully opened, upper and lower surfaces: Close to 157D; color does not change with development.

*Petals, sterile flowers*.—Quantity and arrangement: About four or five in a single whorl. Length: About 1.5 mm. Width: About 1 mm. Shape: Ovate. Apex: Acute. Base: Cuneate. Margin: Entire. Texture, upper and lower surfaces: Smooth, glabrous. Color: When opening, upper and lower surfaces: Close to 149D. Fully opened, upper and lower surfaces: Close to 149D; color does not change with development.

*Sepals, fertile flowers*.—Quantity and arrangement: About four or five in a single whorl. Length: About 1 mm. Width: About 1 mm. Shape: Ovate. Apex: Acute. Base: Obtuse. Margin: Entire. Texture, upper and lower surfaces: Smooth, glabrous. Color: When opening, upper and lower surfaces: Close to 145B. Fully opened, upper and lower surfaces: Close to 145C; color does not change with development.

*Sepals, sterile flowers*.—Quantity and arrangement: About four or five in a single whorl. Length: About 1.5 cm to 2 cm. Width: About 1 cm to 1.5 cm. Shape: Elliptic to oval. Apex: Obtuse. Base: Obtuse. Margin: Entire. Texture, upper and lower surfaces: Smooth, glabrous. Color: When opening, upper and lower surfaces: Close to 145A. Fully opened, upper surface: Close to 145D; color does not change with development. Fully opened, lower surface: Close to 145C; color does not change with development.

*Pedicels, fertile flowers*.—Length: About 3 mm. Diameter: About 1.5 mm. Strength: Strong. Aspect: Mostly upright. Texture: Smooth, glabrous. Color: Close to 145C.

*Pedicels, sterile flowers*.—Length: About 1.5 cm to 2 cm. Diameter: About 2 mm. Strength: Strong. Aspect: About 80° to 90° from branch axis. Texture: Smooth, glabrous. Color: Close to 145D.

*Reproductive organs, fertile flowers*.—Stamens: Quantity per flower: About nine to ten. Filament length: About 3 mm. Filament color: Close to 157D. Anther length: About 1 mm. Anther shape: Round. Anther color: Close to 145D. Pollen amount: Scarce. Pollen color: Close to 145D. Pistils: Pistil quantity per flower: One. Pistil length: About 0.5 mm to 1 mm. Stigma shape: Two to three-lobed. Stigma color: Close to 146C. Style length: About 0.5 mm. Style color: Close to 146C.

*Reproductive organs, sterile flowers*.—Stamens: Quantity per flower: About eight to ten. Filament length: About 3 mm. Filament color: Close to 157D. Anther length: About 1 mm. Anther shape: Round. Anther color: Close to 157D. Pollen amount: Scarce. Pollen color: Close to 157D. Pistils: Pistil development has not been observed on sterile flowers of the new *Hydrangea* to date.

*Seeds, only produced by fertile flowers*.—Quantity per fertile flower: About 20 to 30. Length: Less than 0.5 mm. Diameter: Less than 0.5 mm. Color: Close to 200C.

Pathogen & pest resistance: Under commercial production conditions, plants of the new *Hydrangea* have not been observed to be resistant to pathogens and pests common to *Hydrangea* plants to date.

Garden performance: Plants of the new *Hydrangea* have been shown to have good garden performance and to be tolerant to temperatures ranging from about −38° C. to about 38° C.

It is claimed:

1. A new and distinct *Hydrangea* plant named 'HP217903' as illustrated and described.

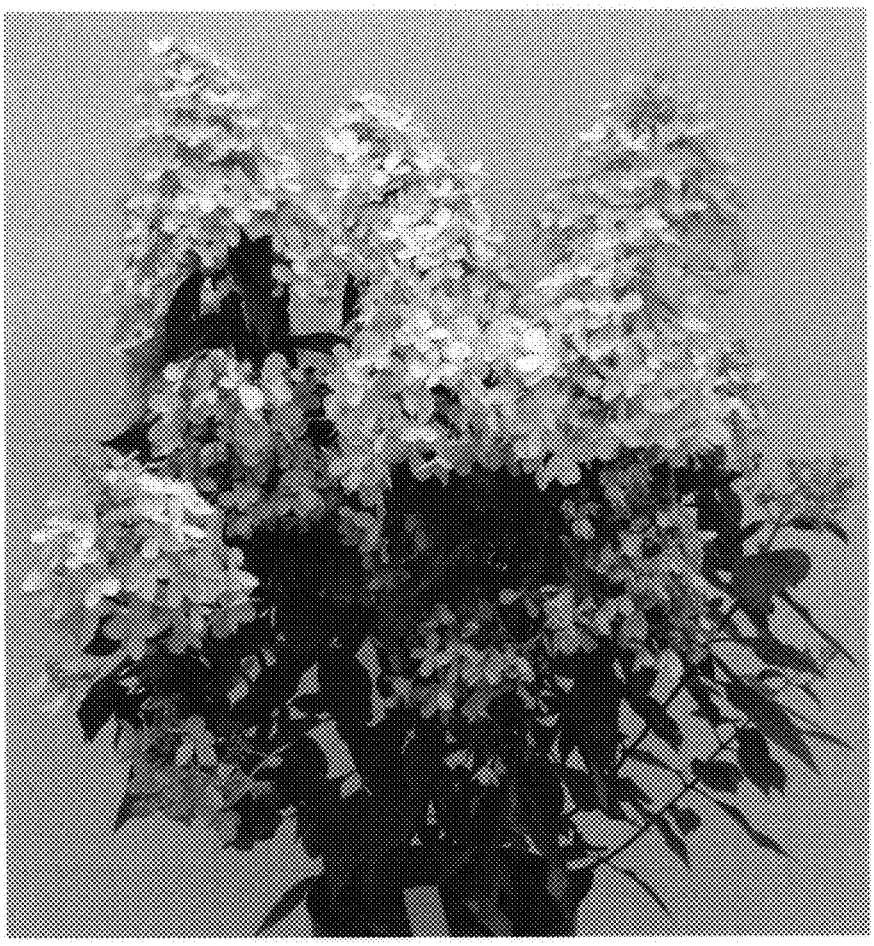

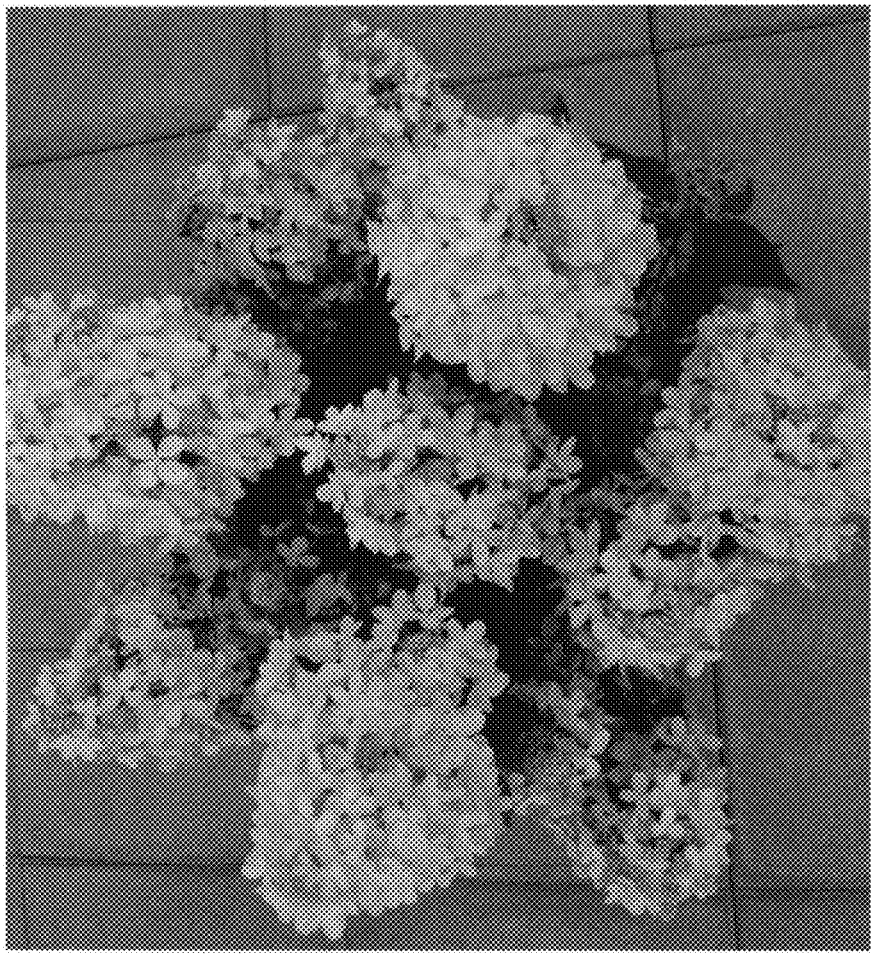

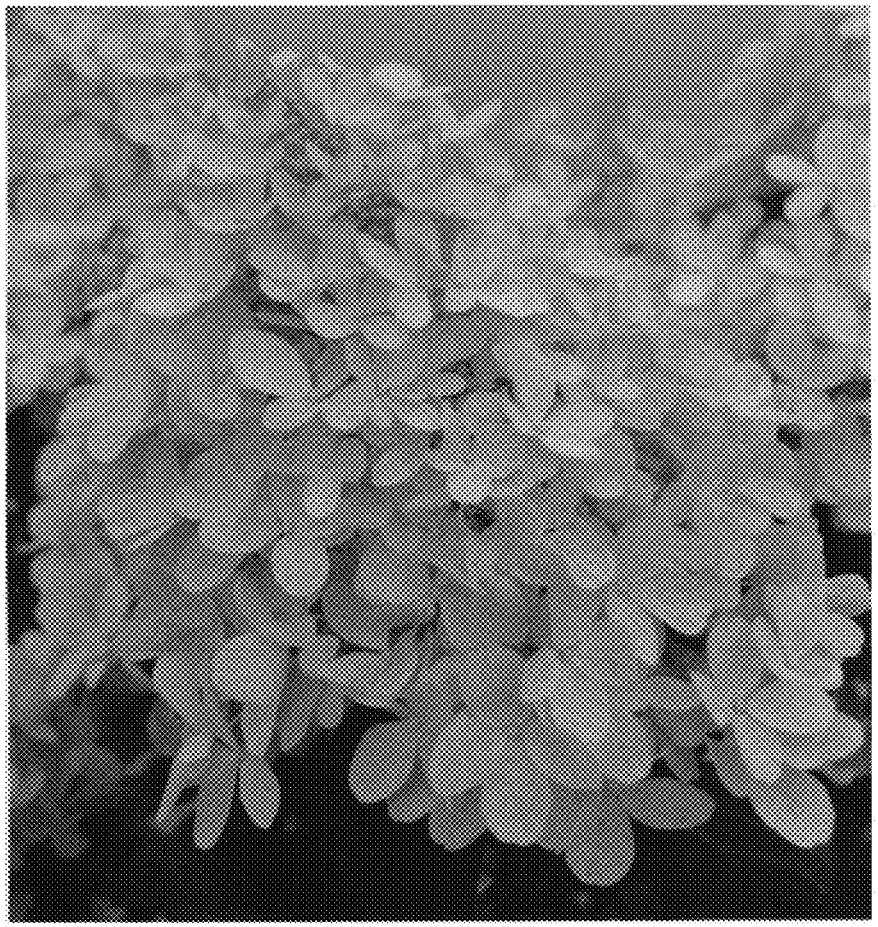

* * * * *